(12) United States Patent
Dutta et al.

(10) Patent No.: US 6,702,849 B1
(45) Date of Patent: *Mar. 9, 2004

(54) METHOD OF PROCESSING OPEN-CELLED MICROCELLULAR POLYMERIC FOAMS WITH CONTROLLED POROSITY FOR USE AS VASCULAR GRAFTS AND STENT COVERS

(75) Inventors: Debashis Dutta, Santa Clara, CA (US); Chicheng Wang, Sunnyvale, CA (US); Kondapavulur T. V. Rao, San Jose, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/460,271
(22) Filed: Dec. 13, 1999
(51) Int. Cl.[7] .................................................. A61F 2/06
(52) U.S. Cl. ...................................................... 623/1.42
(58) Field of Search .......................... 606/1, 108, 194, 606/198, 195; 623/1.1, 1.11, 1.13, 1.39, 1.4, 1.42, 1.46, 12; 427/2.26, 228, 2.3

(56) References Cited

U.S. PATENT DOCUMENTS

| | | |
|---|---|---|
| 4,346,028 A | 8/1982 | Griffith |
| 4,441,215 A | 4/1984 | Kaster |
| 4,473,665 A | 9/1984 | Martini-Vvedensky et al. |
| 4,573,242 A | 3/1986 | Lankton et al. |
| 4,633,873 A | 1/1987 | Dumican et al. |
| 4,640,320 A | 2/1987 | Avison et al. |
| 4,669,474 A | 6/1987 | Barrows |
| 4,718,907 A | 1/1988 | Karwoski et al. |

(List continued on next page.)

FOREIGN PATENT DOCUMENTS

| | | |
|---|---|---|
| EP | 0311065 | 4/1988 |
| EP | 0382014 | 8/1990 |
| EP | 0499299 | 8/1992 |
| EP | 0551182 | 7/1993 |
| EP | 0578998 | 3/1994 |

(List continued on next page.)

OTHER PUBLICATIONS

"Novel Approach to Fabricate Porous Sponges of Poly(D, L–Lactic–Co–Glycolic Acid) Without the Use of Organic Solvents" David J. Mooney, Daniel F. Baldwin, Nam P. Suh, Joseph P. Vacanti and Robert Langer, Biomaterials 17 (1996) 1417–1422.

(List continued on next page.)

*Primary Examiner*—Michael J. Milano
*Assistant Examiner*—(Jackie) Tan-Uyen T. Ho
(74) *Attorney, Agent, or Firm*—Fulwider Patton Lee & Utecht, LLP

(57) ABSTRACT

Porous vascular grafts and stent covers are formed of open-celled microcellular polymeric foams having a porosity that can be modified to be adapted for carrying and delivering different types of therapeutic drugs. A stent cover is formed of a tubular member including at least one layer of a porous, microcellular foam formed from a polymeric material capable of absorbing and releasing therapeutic drugs at predictable rates for delivery of the therapeutic drugs in localized drug therapy in a blood vessel. A composite metal and polymer vascular graft is formed of an interior structural stent member, and an outer layer or coating of the porous, microcellular foam. The method of making the composite metal and polymer vascular graft involves providing an interior structural stent member with an outer layer or coating of the porous, microcellular foam, and can further comprise the step of loading a therapeutic drug into the outer layer of the porous, microcellular foam for delivery of the therapeutic drugs in localized drug therapy in a blood vessel.

33 Claims, 1 Drawing Sheet

U.S. PATENT DOCUMENTS

| | | |
|---|---|---|
| 4,752,054 A | 6/1988 | Jönsson |
| 4,768,507 A | 9/1988 | Fischell et al. |
| 4,776,337 A | 10/1988 | Palmaz |
| 4,813,416 A | 3/1989 | Pollak et al. |
| 4,816,339 A | 3/1989 | Tu et al. |
| 4,866,816 A | 9/1989 | Caveney |
| 4,877,030 A | 10/1989 | Beck et al. |
| 4,878,906 A | 11/1989 | Lindemann et al. |
| 4,879,135 A | 11/1989 | Greco et al. |
| 4,902,290 A | 2/1990 | Fleckenstein et al. |
| 4,950,285 A | 8/1990 | Wilk |
| 4,986,831 A | 1/1991 | King et al. |
| 5,007,926 A | 4/1991 | Derbyshire |
| 5,059,166 A | 10/1991 | Fischell et al. |
| 5,059,211 A | 10/1991 | Stack et al. |
| 5,062,829 A | 11/1991 | Pryor et al. |
| 5,064,435 A | 11/1991 | Porter |
| 5,078,736 A | 1/1992 | Behl |
| 5,084,065 A | 1/1992 | Weldon et al. |
| 5,085,629 A | 2/1992 | Goldberg et al. |
| 5,100,429 A | 3/1992 | Sinofsky et al. |
| 5,104,403 A | 4/1992 | Brotzu et al. |
| 5,108,755 A | 4/1992 | Daniels et al. |
| 5,116,360 A | 5/1992 | Pinchuk et al. |
| 5,123,917 A | 6/1992 | Lee |
| 5,147,385 A | 9/1992 | Beck et al. |
| 5,156,620 A | 10/1992 | Pigott |
| 5,156,623 A | 10/1992 | Hakamatsuka et al. |
| 5,158,548 A | 10/1992 | Lau et al. |
| 5,160,674 A | 11/1992 | Colton et al. |
| 5,163,951 A | 11/1992 | Pinchuk et al. |
| 5,180,366 A | 1/1993 | Woods |
| 5,192,310 A | 3/1993 | Herweck et al. |
| 5,192,311 A | 3/1993 | King et al. |
| 5,195,984 A | 3/1993 | Schatz |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,258,020 A | 11/1993 | Froix |
| 5,279,594 A | 1/1994 | Jackson |
| 5,282,823 A | 2/1994 | Schwartz et al. |
| 5,289,831 A | 3/1994 | Bosley |
| 5,290,271 A | 3/1994 | Jernberg |
| 5,304,220 A | 4/1994 | Maginot |
| 5,306,286 A | 4/1994 | Stack et al. |
| 5,312,339 A | 5/1994 | Boussignac et al. |
| 5,330,500 A | 7/1994 | Song |
| 5,334,201 A | 8/1994 | Cowan |
| 5,337,503 A | 8/1994 | Goby |
| 5,342,348 A | 8/1994 | Kaplan |
| 5,342,621 A | 8/1994 | Eury |
| 5,344,426 A | 9/1994 | Lau et al. |
| 5,344,444 A | 9/1994 | Glastra |
| 5,354,329 A | 10/1994 | Whalen |
| 5,356,423 A | 10/1994 | Tihon et al. |
| 5,356,433 A | 10/1994 | Rowland et al. |
| 5,383,925 A | 1/1995 | Schmitt |
| 5,383,928 A | 1/1995 | Scott et al. |
| 5,385,580 A | 1/1995 | Schmitt |
| 5,422,377 A * | 6/1995 | Aubert .................. 521/64 |
| 5,441,515 A | 8/1995 | Khosravi et al. |
| 5,449,382 A | 9/1995 | Dayton |
| 5,551,954 A | 9/1996 | Buscemi et al. |
| 5,605,696 A | 2/1997 | Eury et al. |
| 5,624,411 A | 4/1997 | Tuch |
| 5,626,562 A * | 5/1997 | Castro .................. 604/508 |
| 5,649,977 A | 7/1997 | Campbell |
| 5,713,920 A * | 2/1998 | Bezwada et al. |
| 5,718,726 A * | 2/1998 | Amon et al. .................. 128/898 |
| 5,763,502 A * | 6/1998 | Barker et al. .................. 521/174 |
| 5,823,198 A * | 10/1998 | Jones et al. .................. 128/899 |
| 5,873,904 A * | 2/1999 | Ragheb et al. .................. 623/1.13 |
| 5,968,093 A * | 10/1999 | Kranz .................. 623/1.15 |
| 5,969,020 A | 10/1999 | Shalaby et al. |
| 6,027,795 A * | 2/2000 | Kabra et al. .................. 428/305.5 |
| 6,096,070 A * | 8/2000 | Ragheb et al. .................. 604/265 |
| 6,099,562 A * | 8/2000 | Ding et al. .................. 623/1.46 |
| 6,255,408 B1 * | 7/2001 | Shalaby |
| 6,281,256 B1 * | 8/2001 | Harris et al. .................. 521/51 |
| 6,299,604 B1 * | 10/2001 | Ragheb et al. .................. 604/265 |
| 6,355,699 B1 * | 3/2002 | Vyakarnam et al. .................. 521/61 |
| 6,358,556 B1 * | 3/2002 | Ding et al. .................. 427/2.24 |
| 6,391,052 B2 * | 5/2002 | Buirge et al. .................. 623/1.47 |
| 6,432,126 B1 * | 8/2002 | Gambale et al. .................. 623/1.1 |
| 6,482,227 B1 * | 11/2002 | Solovay .................. 623/1.13 |

FOREIGN PATENT DOCUMENTS

| | | |
|---|---|---|
| EP | 0604022 | 6/1994 |
| EP | 0621017 | 10/1994 |
| EP | 0716835 | 6/1996 |
| EP | 0716836 | 6/1996 |
| EP | 0 756 853 A1 | 2/1997 |
| EP | 0 847 733 A1 | 6/1998 |
| EP | 0 875 217 A2 A3 | 11/1998 |
| FR | 2673843 | 9/1992 |
| FR | 2694688 | 2/1994 |
| WO | WO 90/06094 | 6/1990 |
| WO | 94/13268 | 6/1994 |
| WO | 9421196 | 9/1994 |
| WO | WO 01/40348 A2 | 6/2001 |

OTHER PUBLICATIONS

"Release of Heparin from Polycaprolactone Films for Intravascular Stents," E. Mathiowitz et al., 1994 Proceedings of the 21$^{st}$ Int'l Symposium on Controlled Release of Bioactive Materials, Controlled Release Society, Inc. pp. 272–273.

"Percolation Effects in Controlled Release Matrices," J.D. Bonny and H. Leuenberger, Proceed. Intern. Symp. on Control. Rel. of Bioact. Mater., 18 (1991), Controlled Release Society, Inc., pp. 407–408.

Hot–Melt Extruded Pellets for the Sustained Release of Highly Dosed Freely Soluble Drugs, Nicolas Follonier et al., Proceed. Intern. Symp. on Control. Rel. of Bioact. Mater., 18 (1991), Controlled Release Society, Inc., pp. 578–579.

"Protein Release From Poly(L–Lactic Acid)/Pluronic Blends," Tae Gwan Park et al., Proceed. Intern. Symp. on Control. Rel. of Bioact. Mater., 18 (1991), Controlled Release Society, Inc., pp. 682–683.

"Poly(ethylene oxide) (PEO) and Different Molecular Weight PEO Blends Monolithic Devices for Drug Release," A. Apicella et al., Biomaterials 1993, Vol 14, No. 2, pp. 83–90.

"Polymers for Sustained Release of Macromolecules," Nicholas A. Peppas and Richard Korsmeyer, Polymer News, 1980, vol. 6, pp. 149–150.

"Polymeric Membranes and Matrices in Drug Dosage Form Design," M. Nakano, Journal of Membrane Scient, 5 (1979) pp. 355–370.

"Polymers for Sustained Macromolecule Release: Procedures for Fabricate Reproducible Delivery Systems and Control Release Kinetics," W.D. Rhine et al., Journal of Pharmaceuticl Sciences, Vol 69, No. 3, Mar. 1980, pp. 265–270.

"A Polymeric Controlled Drug Delivery Device for Peptides Based on a Surface Desorption/Diffusion Mechanism," G.J. Boer and J. Kruisbrink, (1986), 10 pgs.

"A Model of Dissolution–Controlled Solute Relese from Porous Drug Delivery Polymeric Systems," Nikolaos A. Peppas, Journal of Biomedical Materials Research, vol. 17, 1079–1087 (1983), pp. 1079–1087.

"Diffusion in Porous Materials Above the Percolation Threshold," Jayne E. Hastedt and James L. Wright, Pharmaceutical Research, vol. 7, No. 9, 1990, pp. 893–901.

Microporous Membrane–Coated Tablets Prepared With Aqueous Latexes, R. Boadmeier and O. Paeratakul, Proceed. Intern. Symp. Control. Rel. Bioact. Mater., 16, (1989), p. 68.

* cited by examiner

METHOD OF PROCESSING OPEN-CELLED MICROCELLULAR POLYMERIC FOAMS WITH CONTROLLED POROSITY FOR USE AS VASCULAR GRAFTS AND STENT COVERS

BACKGROUND OF THE INVENTION

1. Field of the Invention

This invention relates generally to expandable intraluminal vascular grafts and stents, and more particularly concerns grafts and stents coated or covered with an open-celled microcellular polymeric foam component capable of carrying and releasing therapeutic drugs, and a method of incorporating therapeutic drugs into the open-celled microcellular polymeric foam component of such grafts and stents.

2. Description of Related Art

Vascular grafts and stents are vascular interventional devices that are typically implanted within a vessel in a contracted state and expanded when in place in the vessel in order to maintain patency of the vessel to allow fluid flow through the vessel. Ideally, implantation of such vascular interventional devices is accomplished by moving the device along a guide wire previously placed in the vessel, and expanding and locking the device in an expanded state by inflation of a balloon within the device. The graft or stent can then be left in place by deflating the balloon and removing the guide wire. However, restenosis of blood vessels, such as coronary vessels treated with percutaneous transluminal coronary angioplasty (PTCA) or stents is a current clinical challenge. To address this problem, various approaches are being developed to reduce restenosis by locally delivering drugs to the target site of possible restenosis.

Stents commonly have a metallic structure to provide the strength required to function as a stent, but commonly have been unable to satisfactorily deliver localized therapeutic pharmacological agents to a blood vessel at the location being treated with the stent. While polymeric materials that can be loaded with and release drugs or other pharmacological treatments can be used for drug delivery, polymeric materials may not fulfill the structural and mechanical requirements of a stent, especially when the polymeric materials are loaded with a drug, since drug loading of a polymeric material can significantly affect the structural and mechanical properties of the polymeric material. Since it is often useful to provide localized therapeutic pharmacological treatment of a blood vessel at the location being treated with the stent, it would be desirable to provide a polymeric component for grafts and stents to provide the capability of being loaded with therapeutic drugs, to function together with the graft or stent for placement and release of the therapeutic drugs at a specific intravascular site.

Commonly used grafts in the industry are formed from expanded polytetrafluoroethylene (ePTFE), and knitted polyesters such as Dacron. However, the use of grafts formed with such polymeric material is typically restricted to larger vessels greater than about four millimeters in diameter. When used with narrower blood vessels, these types of grafts tend to become occluded. Moreover, the compliance of such grafts commonly does not match that of natural artery. In recent years, improved polymers such as polyurethanes containing carbonate linkages, such as that available under the trade name "CARBOTHANE" from The Carboline Company of St. Louis, Mo., and the material available under the trade name "CHRONOFLEX" from CardioTech International, Inc. of Woburn, Mass., have been developed for use in forming small bore vascular grafts. The mechanical characteristics of these grafts are close to that of natural arteries.

Such a polymeric component for use in forming vascular grafts and stent covers capable of carrying and delivering therapeutic drugs should have a microporous, open-celled structure, because the porosity not only allows the material to carry and deliver therapeutic drugs, but also permits ingrowth into the material of cells and capillaries that take part in the healing process, and can nurture the pseudointima. Currently, process techniques that have commonly been employed to make these polymers microporous include laser drilling of holes in the polymer tubing, and extrusion of the polymeric material with blowing agents, which may be chemicals or gas, to create cells in the extruded tubing. Laser drilling of such material produces holes in the material, while extrusion with blowing agents commonly results in large non-uniform cells on the order of millimeters in diameter. However, conventional foaming techniques that use blowing agents, either using chemical blowing agents or gas assisted blowing agents, do not typically result in an open-celled reticulated structure with an accurately controlled, uniform cell size.

Microcellular polymeric foams are also known that are characterized by cell sizes in the range of 0.1 to 100 microns, with cell densities in the range of $10^9$ to $10^{15}$ cells per cubic cm. Typically, such microcellular polymeric foams exhibit properties comparable or superior to properties of structural foams, and, in some cases to the unfoamed polymer. Suitable microcellular foams are currently preferably produced by exposure of the thermoplastic polymer to super-critical $CO_2$ fluid under high temperature and pressure to saturate the thermoplastic polymer with the super-critical $CO_2$ fluid, and then cooling the thermoplastic polymer to foam the amorphous and semi-crystalline thermoplastic polymers. Such suitable microcellular foams can be produced as described in U.S. Pat. Nos. 4,473,665 and 5,160,674, incorporated herein by reference in their entirety. The foaming process can be carried out on extruded polymer tubing of the proper dimension. The first stage of microcellular foam processing involves dissolving an inert gas, such as nitrogen or $CO_2$, under pressure into the polymer matrix. The next phase is the rapid creation of microvoids. This is initiated by inducing large thermodynamic instability. The thermodynamic instability is induced by quickly decreasing the solubility of the gas in the polymer by changing the pressure or temperature.

There remains a need for vascular grafts and stent covers having a porosity that can be controlled to be suitable for the types of therapeutic drugs to be carried and delivered to a target site to be treated. The present invention meets this and other needs.

SUMMARY OF THE INVENTION

Briefly, and in general terms, the present invention provides for improved porous vascular grafts and stent covers formed of open-celled microcellular polymeric foams having a porosity that can be modified to be adapted for carrying and delivering different types of therapeutic drugs. The morphology of the open-celled microcellular polymeric foams, including the openness, cell size and porosity of the foams, can be controlled so that the cell sizes can be made very uniform, and can be controlled precisely by changing thermodynamic variables like pressure and temperature during formation of the open-celled microcellular polymeric foams. The open-celled microcellular polymeric foams can be formed by a batch process that can be easily controlled and operated, in which extruded tubing can be cut to the desired lengths and then foamed in separate pressure chamber.

The invention accordingly provides for a stent cover that can be used to carry and deliver therapeutic drugs or as an overcoat barrier layer to control drug release by a drug-coated stent. In one presently preferred embodiment, such a stent cover comprises a tubular member for use with a stent, the stent cover including at least one layer of a porous, microcellular foam formed from a polymeric material capable of absorbing and releasing therapeutic drugs at predictable rates for delivery of the therapeutic drugs in localized drug therapy in a blood vessel. The layer of porous, microcellular foam can range in thickness from about a few nanometers to a millimeter, and the diameter of the pores and the amount of porosity in the foam can be adjusted according to the molecular weight of the drug compound. The diameter of the pores or cells of the microcellular foam can, for example, be made as small as about a few nanometers to accommodate low molecular weight compounds with molecular weights in the range of 10–1,000 daltons up to large molecular weight compounds with molecular weight in the range of 1,000 to 100,000 daltons, as well as supra molecular structures with molecular weights greater than 100,000 daltons. The polymeric material from which the microcellular foam can be formed include polyurethanes containing carbonate linkages, and biodegradable polymers such as poly-L-lactic acid (PLLA), poly-DL-lactic acid (DL-PLA), polyglycolic acid (PGA), p-dioxanone, and tri-methylene carbonate/glycolic acid copolymers (TMC/PGA), for example, although other similar materials may also be suitable. Examples of supra molecular structures include viral particles used for gene therapy, liposomes, ribozymes, and the like.

In another aspect, the invention also provides for a composite metal and polymer vascular graft or coated stent, comprising an interior structural stent member, and an outer layer or coating of a porous, microcellular foam formed from a polymeric material capable of absorbing and releasing therapeutic drugs at predictable rates for delivery of the therapeutic drugs in localized drug therapy in a blood vessel. In a currently preferred embodiment, the stent can be formed of a metal such as stainless steel, tantalum, a composite of tantalum and silicon carbide, gold, or can be formed of a polymer, or of a composite. Other metals that may also be suitable for forming the stent include nickel-titanium alloy, platinum-iridium alloy, molybdenum-rhenium alloy, gold, magnesium, and combinations thereof. The porous, microcellular foam can range in thickness from about a few nanometers to a millimeter, and the diameter of the pores and the amount of porosity in the foam can be adjusted according to the molecular weight of the drug compound. The diameter of the pores or cells of the microcellular foam can, for example, be made as small as about a few nanometers to accommodate low molecular weight compounds with molecular weights in the range of 10–1,000 daltons up to large molecular weight compounds with molecular weight in the range of 1,000 to 100,000 daltons and supramolecular structures with molecular weights greater than 100,000 daltons. The polymeric material from which the microcellular foam can be formed include polyurethanes containing carbonate linkages, and biodegradable polymers such as poly-L-lactic acid (PLLA), poly-DL-lactic acid (DL-PLA), polyglycolic acid (PGA), p-dioxanone, and trimethylene carbonate/glycolic acid copolymers (TMC/PGA), for example, although other similar materials may also be suitable. Examples of supra molecular structures include viral particles used for gene therapy, liposomes, ribozymes, and the like.

In another aspect, the present invention also provides for a method of making a composite metal and polymer vascular graft or coated stent, including an interior structural stent member and an outer layer or coating of a porous, microcellular foam formed from a polymeric material capable of absorbing and releasing therapeutic drugs at predictable rates for delivery of the therapeutic drugs in localized drug therapy in a blood vessel, comprising the steps of providing a stent, and coating the stent with an outer layer or coating of a porous, microcellular foam formed from a polymeric material capable of absorbing and releasing therapeutic drugs at predictable rates for delivery of the therapeutic drugs in localized drug therapy in a blood vessel. In another aspect, the method can further comprise the step of loading a therapeutic drug into the outer layer or coating of a porous, microcellular foam for delivery of the therapeutic drugs in localized drug therapy in a blood vessel. The porous, microcellular foam can be formed with different thicknesses, pore sizes, pore distributions, and pore-size gradients to control drug release or pharmacokinetics, as desired.

Preferred examples of therapeutic drugs or pharmacologic compounds that may be loaded into the outer layer of the composite metal and polymer vascular graft or coated stent or into the stent cover and delivered to the target site in the vasculature, or loaded onto the stent over which the stent cover is to be disposed for controlling the drug release of the drug coated stent include taxol, aspirin, prostaglandins, and the like. Therapeutic agents that may also be suitable for loading into the stent cover or for moderation of drug release from the covered stent may also include, for example, antiplatelets, antithrombins, cytostatic or antiproliferative agents, sodium heparin, low molecular weight heparin, hirudin, argatroban, forskolin, vapiprost, prostacyclin and prostacyclin analogues, dextran, D-phe-pro-arg-chloromethylketone, dipyridamole, glycoprotein IIb/IIIa platelet membrane receptor antibody, recombinant hirudin, thrombin inhibitor, angiopeptin, angiotensin converting enzyme inhibitors, Lisinopril, and cisplatin; anti-inflammatories such as steroids; anti-cancer compounds such as taxon and actinomycin; macromolecules such as peptides, proteins, genes and antisense compounds; calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, serotonin blockers, thio-protease inhibitors, triazolopyrimidine and other PDGF antagonists, alpha-interferon and genetically engineered epithelial cells, supramolecular weight structures with molecular weights greater than 100,000 daltons, and up to about 1,000,000 daltons, including viral particles used for gene therapy, ribozymes and liposomes, and combinations thereof.

These and other aspects and advantages of the invention will become apparent from the following detailed description and the accompanying drawings, which illustrate by way of example the features of the invention.

DETAILED DESCRIPTION OF THE PREFERRED EMBODIMENTS

Stents commonly have a metallic structure to provide the strength required to function as a stent, while polymeric materials are typically used for loading and release of drugs or other pharmacological treatments for drug delivery. Vascular grafts can be made of polymers such as polyurethanes containing carbonate linkages, but such polymeric components used in forming components of stents or vascular grafts capable of carrying and delivering therapeutic drugs typically do not have a microporous, open-celled structure, and conventional techniques for forming foamed polymeric materials typically do not result in an open-celled reticulated structure with an accurately controlled, uniform cell size.

Figure 1:
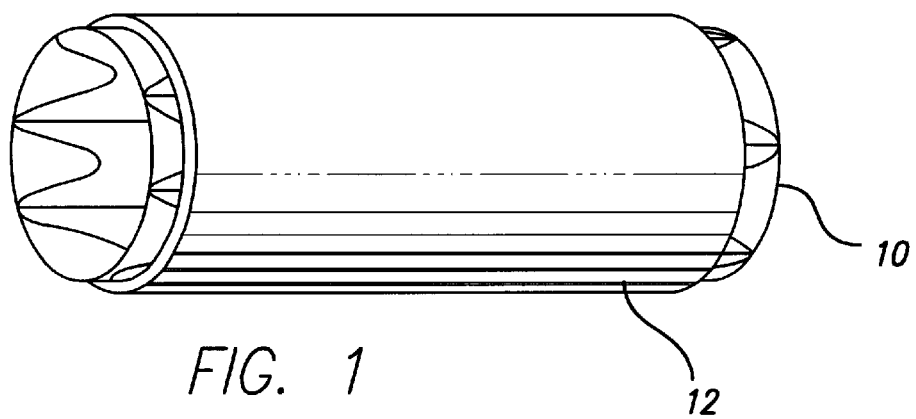
FIG. 1 is a perspective view of a combination of a stent and stent cover according to the present invention.
Figure 2:
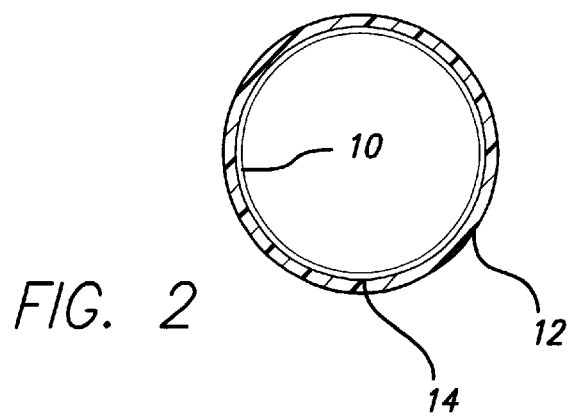
FIG. 2 is a cross-sectional view taken along line 2—2 of FIG. 1.

As is illustrated in the drawings, the invention is embodied in improved porous vascular grafts and stent covers formed of open-celled microcellular polymeric foams having a porosity adapted for carrying and delivering different types of therapeutic drugs. Referring to FIGS. 1 and 2, in a currently preferred embodiment, the invention provides for a stent cover that can be used to carry and deliver therapeutic drugs or as an overcoat barrier layer to control drug release by a drug-coated stent such as stent 10. The stent can be of the type that is expanded by a balloon member or other similar device, or of the type that is self-expanding, and can have virtually any pattern known from prior art stents. In a currently preferred embodiment, the stent can be formed of a metal such as stainless steel, tantalum, a composite of tantalum and silicon carbide, gold, or can be formed of a polymer, or of a composite. Other metals that may also be suitable for forming the stent include nickel-titanium alloy, platinum-iridium alloy, molybdenum-rhenium alloy, gold, magnesium, and combinations thereof.

In a currently preferred embodiment, the stent cover 12 comprises a tubular member adapted to be mounted over the stent. As shown in FIGS. 1 and 2, the stent cover includes at least one layer 14 of a porous, microcellular foam formed from a polymeric material capable of absorbing and releasing therapeutic drugs at predictable rates for delivery of the therapeutic drugs in localized drug therapy in a blood vessel. The layer of porous, microcellular foam can range in thickness from about a few nanometers to a millimeter, and the diameter of the pores and the amount of porosity in the foam can be adjusted according to the molecular weight of the drug compound.

Microcellular foams are typically characterized by cell sizes or diameters in the range of 0.1 to 100 microns, and cell densities in the range of $10^9$ to $10^{15}$ cells per cubic cm. Typically, microcellular plastics exhibit comparable or superior properties to structural foams, and, in some cases to the unfoamed polymer. Microcellular foams can be formed based upon the process developed at MIT and Clarkson Univ., as outlined in V. Kumar and N. P. Suh, Polym. Eng. Sci., 30, pp. 1323–1329, (1990), and C. Wang, K. Cox and G. Campbell, J. Vinyl Additives Tech., 2(2), pp. 167–169 (1996).

The foaming process can be carried out on polymer preforms such as extruded polymer tubing of the desired dimension. The first stage of microcellular foam processing involves dissolving an inert gas, such as nitrogen or $CO_2$, under pressure into the polymer matrix. The next phase is the rapid creation of microvoids. This is initiated by inducing large thermodynamic instability. The thermodynamic instability is induced by quickly decreasing the solubility of the gas in the polymer by changing the pressure or temperature.

The diameter of the pores or cells of the microcellular foam can, for example, be made as small as about a few nanometers to accommodate low molecular weight compounds with molecular weights in the range of 10–1,000 daltons up to large molecular weight compounds with molecular weight in the range of 1,000 to 100,000 daltons. The polymeric material from which the microcellular foam can be formed include polyurethanes containing carbonate linkages, and biodegradable polymers such as poly-L-lactic acid (PLLA), poly-DL-lactic acid (DL-PLA), polyglycolic acid (PGA), p-dioxanone, and trimethylene carbonate/glycolic acid copolymers (TMC/PGA), for example, although other similar materials may also be suitable.

The morphology of the open-celled microcellular polymeric foams, including the openness, cell size and porosity of the foams, can be controlled so that the cell sizes can be made very uniform, and can be controlled precisely by changing thermodynamic variables like pressure and temperature during formation of the open-celled microcellular polymeric foams. The open-celled microcellular polymeric foams can be formed by a batch process that can be easily controlled and operated, in which extruded tubing can be cut to the desired lengths and then foamed in separate pressure chamber.

Figure 3:
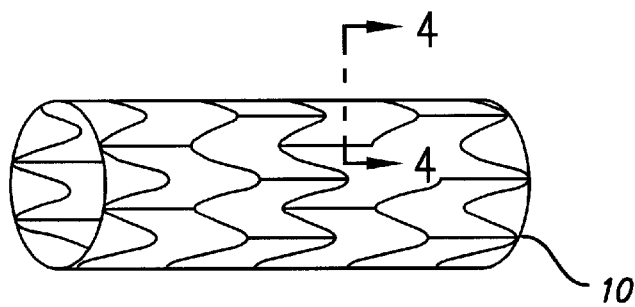
FIG. 3 is a perspective view of a composite metal and polymer vascular graft or coated stent according to the present invention.
Figure 4:
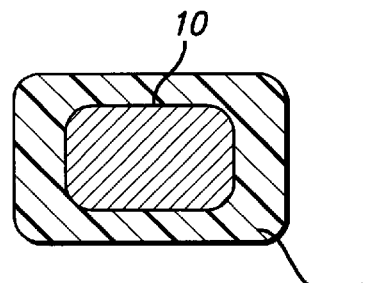
FIG. 4 is a cross-sectional view of an element of the composite metal and polymer vascular graft or coated stent taken along line 4—4 of FIG. 3.

In another presently preferred embodiment illustrated in FIGS. 3 and 4, the invention provides for a composite metal and polymer vascular graft or coated stent, comprising an interior structural stent member 10, and an outer layer or coating of a porous, microcellular foam 16 formed from a polymeric material capable of absorbing and releasing therapeutic drugs at predictable rates for delivery of the therapeutic drugs in localized drug therapy in a blood vessel. The composite metal and polymer vascular graft or coated stent, can be formed by providing a stent member 10, and coating the stent with an outer layer or coating of a porous, microcellular foam formed from a polymeric material capable of absorbing and releasing therapeutic drugs at predictable rates for delivery of the therapeutic drugs in localized drug therapy in a blood vessel. This can be accomplished by coating the stent member with a polymer matrix in which an inert gas, such as nitrogen or $CO_2$, is dissolved under pressure. The creation of microvoids to form the microcellular foam can be accomplished by quickly decreasing the solubility of the gas in the polymer matrix coated on the stent member by changing the pressure or temperature. As noted above, the porous, microcellular foam can range in thickness from about a few nanometers to a millimeter, and the diameter of the pores and the amount of porosity in the foam can be adjusted according to the molecular weight of the drug compound. The diameter of the pores or cells of the microcellular foam can, for example, be made as small as about a few nanometers to accommodate low molecular weight compounds with molecular weights in the range of 10–1,000 daltons up to large molecular weight compounds with molecular weight in the range of 1,000 to 100,000 daltons. The polymeric material from which the microcellular foam can be formed include polyurethanes containing carbonate linkages, and biodegradable polymers such as poly-L-lactic acid (PLLA), poly-DL-lactic acid (DL-PLA), polyglycolic acid (PGA), p-dioxanone, and trimethylene carbonate/glycolic acid copolymers (TMC/PGA), for example, although other similar materials may also be suitable.

In another currently preferred embodiment, a therapeutic drug can be loaded into the outer layer or coating 16 of porous, microcellular foam for delivery of the therapeutic drugs in localized drug therapy in a blood vessel. The porous, microcellular foam can be formed with different thicknesses, pore sizes, pore distributions, and pore-size gradients to control drug release or pharmacokinetics, as desired. The stent cover may also be loaded with such therapeutic drugs for a similar purpose in use in combination with a stent. Alternatively, or in addition, particularly when the stent is formed of a suitable material, the stent may also be drug loaded. Preferred examples of therapeutic drugs or pharmacologic compounds that may be loaded, for controlling the release of the drug include taxol, aspirin, prostaglandins, and the like. Therapeutic agents that may also be suitable for loading into the stent cover or for moderation of drug release from the covered stent may also include, for example, antiplatelets, antithrombins, cytostatic or antiproliferative agents, sodium heparin, low molecular weight heparin, hirudin, argatroban, forskolin, vapiprost, prostacyclin and prostacyclin analogues, dextran, D-phe-pro-arg-chloromethylketone, dipyridamole, glycoprotein IIb/IIIa platelet membrane receptor antibody, recombinant hirudin, thrombin inhibitor, angiopeptin, angiotensin converting enzyme inhibitors, Lisinopril, and cisplatin; anti-inflammatories such as steroids; anti-cancer compounds such as taxon and actinomycin; macromolecules such as peptides, proteins, genes and antisense compounds; calcium channel blockers, colchicine, fibroblast growth factor antagonists, fish oil, omega 3-fatty acid, histamine antagonists, HMG-CoA reductase inhibitor, methotrexate, monoclonal antibodies, nitroprusside, phosphodiesterase inhibitors, prostaglandin inhibitor, serotonin blockers, thioprotease inhibitors, triazolopyrimidine and other PDGF antagonists, alpha-interferon and genetically engineered epithelial cells, supramolecular weight structures with molecular weights greater than 100,000 daltons, and up to about 1,000,000 daltons, including viral particles used for gene therapy, ribozymes and liposomes, and combinations thereof.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A stent cover for use with a stent for controlled release of therapeutic drugs by a stent for delivery of the therapeutic drugs in localized drug therapy in a blood vessel, comprising:

a tubular member formed of at least one layer of a porous, open-celled microcellular foam of a polymeric material formed by dissolving an inert gas in the polymeric material at an initial temperature and pressure and creating microvoids in the polymeric material by changing the pressure or temperature of the polymeric material, said porous open-celled microcellular foam being capable of absorbing and releasing therapeutic drugs at predictable rates.

2. The stent cover of claim 1, wherein the layer of porous, microcellular foam ranges in thickness from about a few nanometers to about a millimeter.

3. The stent cover of claim 1, wherein the size of the pores in the foam and the amount of porosity in the foam is adjusted to accommodate the molecular weight of a desired drug compound.

4. The stent cover of claim 1 wherein the diameter of the pores of the microcellular foam is formed to accommodate a compound having a molecular weight in the range of from about 10 daltons up to about 1,000,000 daltons.

5. The stent cover of claim 1, wherein the microcellular foam is formed from a polymeric material selected from the group consisting of polyurethanes containing carbonate linkages, poly-L-lactic acid, poly-DL-lactic acid, polyglycolic acid, p-dioxanone, and trimethylene carbonate/glycolic acid copolymers.

6. A composite metal and polymer vascular graft for controlled release of therapeutic drugs by a stent for delivery of the therapeutic drugs in localized drug therapy in a blood vessel, comprising:

an inner structural stent member; and an outer layer formed of at least one layer of a porous, open-celled microcellular foam of a polymeric material formed by dissolving an inert gas in the polymeric material at an initial temperature and pressure and creating microvoids in the polymeric material by changing the pressure or temperature of the polymeric material, said porous open-celled microcellular foam being capable of absorbing and releasing therapeutic drugs at predictable rates for delivery of the therapeutic drugs in localized drug therapy in a blood vessel.

7. The composite metal and polymer vascular graft of claim 6, wherein said inner structural stent member is formed a metal selected from the group consisting of stainless steel, tantalum and gold.

8. The composite metal and polymer vascular graft of claim 6, wherein said inner structural stent member is formed a material selected from the group consisting of polymers and composites.

9. The composite metal and polymer vascular graft of claim 6, wherein said inner structural stent member is formed a composite of tantalum and silicon carbide.

10. The composite metal and polymer vascular graft of claim 6, wherein the layer of porous, open-celled microcllular foam ranges in thickness from about a few nanometers to a millimeter.

11. The composite metal and polymer vascular graft of claim 6, wherein the size of the pores in the foam and the amount of porosity in the foam is adjusted to accommodate the molecular weight of a desired drug compound.

12. The composite metal and polymer vascular graft of claim 6, wherein the diameter of the pores of the porous, open-celled microcellular foam is formed to accommodate a compound having a molecular weight in the range of from about 10 daltons up to about 1,000,000 daltons.

13. The composite metal and polymer vascular graft of claim 6, wherein the porous, open-celled microcellular foam is formed from a polymeric material selected from the group consisting of polyurethanes containing carbonate linkages, poly-L-lactic acid, poly-DL-lactic acid, polyglycolic acid, p-dioxanone, and trimethylene carbonate/glycolic acid copolymers.

14. A method of making a composite metal and polymer vascular graft or coated stent, including an inner structural stent member and an outer layer or coating of a porous, open-celled microccllular foam formed from a polymeric material capable of absorbing and releasing therapeutic drugs at predictable rates for delivery of the therapeutic drugs in localized drug therapy in a blood vessel, comprising the steps of:

providing an inner structural stent member; and coating the inner structural stent member with at least one outer layer of a polymeric material, wherein microvoids have been formed in the polymeric material by dissolving an inert gas under pressure in the polymeric material and rapidly changing the temperature or pressure of the polymeric material to form a porous, open-celled microcellular foam from the polymeric material, said porous, open-celled microcellular foam being capable of absorbing and releasing therapeutic drugs at predictable rates for delivery of the therapeutic drugs in localized drug therapy in a blood vessel.

15. The method of claim 14, further comprising the step of adjusting the size of the pores in the foam and the amount of porosity in the foam to accommodate the molecular weight of a desired drug compound.

16. The method of claim 14, wherein the layer of porous, open-celled microcellular foam ranges in thickness from about a few nanometers to about a millimeter.

17. The method of claim 15, wherein the diameter of the pores of the porous, open-celled microcellular foam is formed to accommodate a compound having a molecular weight in the range of from about 10 daltons up to about 1,000,000 daltons.

18. The method of claim 14, wherein the porous, open-celled microcellular foam is formed from a polymeric material selected from the group consisting of polyurethanes containing carbonate linkages, poly-L-lactic acid, poly-DL-lactic acid, polyglycolic acid, p-dioxanone, and trimethylene carbonate/glycolic acid copolymers.

19. The method of claim 14, further comprising the step of loading a therapeutic drug into the outer layer of a porous, open-celled microcellular foam for delivery of the therapeutic drugs in localized drug therapy in a blood vessel.

20. The method of claim 14, wherein the therapeutic drug is selected from the group consisting of taxol, aspirin and prostaglandins.

21. A stent cover for use with a stent for controlled release of a therapeutic drug or agent for delivery of the therapeutic drug or agent in drug therapy in a lumen of a body vessel, comprising:

a tubular member formed of at least one layer of a porous, open-celled microcellular foam of a polymeric material formed by dissolving an inert gas in a preform of the polymeric material at an initial temperature and pressure and creating microvoids in the polymeric material by changing the pressure or temperature of the preform of the polymeric material, said porous open-celled microcellular foam being capable of releasing a therapeutic drug or agent.

22. The stent cover of claim 21, wherein the stent cover is adapted for use in delivery of the therapeutic drug or agent in localized drug therapy.

23. The stent cover of claim 21, wherein said at least one layer of a porous, open-celled microcellular foam of a polymeric material is capable of absorbing the therapeutic drug or agent.

24. The stent cover of claim 21, wherein said at least one layer of a porous, open-celled microcellular foam of a polymeric material is capable of releasing the therapeutic drug or agent at predictable rates.

25. A composite metal and polymer vascular graft for controlled release of a therapeutic drug or agent for delivery of the therapeutic drug or agent in drug therapy in a lumen of a body vessel, comprising:

an inner structural stent member; and an outer layer formed of at least one layer of a porous, open-celled microcellular foam of a polymeric material formed by dissolving an inert gas in a preform of the polymeric material at an initial temperature and pressure and creating microvoids in the preform of the polymeric material by changing the pressure or temperature of the preform of the polymeric material, said porous open-celled microcellular foam being capable of releasing a therapeutic drug or agent.

26. The composite metal and polymer vascular graft of claim 25, wherein the composite metal and polymer vascular graft is adapted for use in delivery of the therapeutic drug or agent in localized drug therapy.

27. The composite metal and polymer vascular graft of claim 25, wherein said at least one layer of a porous, open-celled microcellular foam of a polymeric material is capable of absorbing the therapeutic drug or agent.

28. The composite metal and polymer vascular graft of claim 25, wherein said at least one layer of a porous, open-celled microcellular foam of a polymeric material is capable of releasing the therapeutic drug or agent at predictable rates.

29. A method of making a composite metal and polymer vascular graft or coated stent, including an inner structural stent member and an outer layer or coating of a porous, open-celled microcellular foam formed from a polymeric material capable of releasing a therapeutic drug or agent for delivery of the therapeutic drug or agent in drug therapy in a lumen of a body vessel, comprising the steps of:

providing an inner structural stent member; and coating the inner structural stent member with at least one outer layer of a polymeric material, wherein microvoids have been formed in a preform of the polymeric material by dissolving an inert gas under pressure in the preform of the polymeric material and rapidly changing the temperature or pressure of the preform of the polymeric material to form a porous, open-celled microcellular foam from the preform of the polymeric material capable of releasing a therapeutic drug or agent.

30. The method of claim 29, wherein the composite metal and polymer vascular graft is adapted for use in delivery of the therapeutic drug or agent in localized drug therapy.

31. The method of claim 29, wherein said at least one layer of a porous, open-celled microcellular foam of a polymeric material is capable of absorbing the therapeutic drug or agent.

32. The method of claim 29, wherein said at least one layer of a porous, open-celled microcellular foam of a polymeric material is capable of releasing the therapeutic drug or agent at predictable rates.

33. A stent cover for use with a stent for controlled release of therapeutic drugs by a stent for delivery of the therapeutic drugs in localized drug therapy in blood vessel, comprising:

a tubular member formed of at least one layer of a porous, microcellular foam with an open-celled reticulated structure;

wherein the microcellular foam is formed by dissolving an inert gas in a preform of a polymeric material at an initial temperature and pressure and creating microvoids in the preform of the polymeric material by changing the pressure or temperature of the preform of the polymeric material, said porous open-celled microcellular foam being capable of absorbing and releasing therapeutic drugs at predictable rates.

* * * * *

UNITED STATES PATENT AND TRADEMARK OFFICE
CERTIFICATE OF CORRECTION

PATENT NO. : 6,702,849 B1
DATED : March 9, 2004
INVENTOR(S) : Debashis Dutta, Chicheng Wang and Kondapavulur T. V. Rao It is certified that error appears in the above-identified patent and that said Letters Patent is hereby corrected as shown below:

Column 8,
Line 58, delete "microccllular" and insert -- microcellular --.

Column 10,
Line 5, delete "microccllular" and insert -- microcellular --.

Signed and Sealed this

Thirty-first Day of August, 2004

JON W. DUDAS
*Director of the United States Patent and Trademark Office*